United States Patent
Kim

(10) Patent No.: US 11,427,681 B2
(45) Date of Patent: Aug. 30, 2022

(54) POLYMER COMPOUNDS CONTAINING MULTIPLE HYDROXYL GROUPS, METHODS FOR PRODUCING THE SAME, AND COMPLEX CONTAINING THE SAME

(71) Applicant: Research & Business Foundation Sungkyunkwan University, Suwon-si (KR)

(72) Inventor: Ji Heung Kim, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 336 days.

(21) Appl. No.: 16/750,479

(22) Filed: Jan. 23, 2020

(65) Prior Publication Data

US 2020/0239637 A1 Jul. 30, 2020

(30) Foreign Application Priority Data

Jan. 28, 2019 (KR) .......................... 10-2019-0010340

(51) Int. Cl.
| | |
|---|---|
| *C08J 3/24* | (2006.01) |
| *C08G 73/10* | (2006.01) |
| *A61K 47/34* | (2017.01) |
| *A61L 27/18* | (2006.01) |

(52) U.S. Cl.
CPC .......... *C08G 73/1092* (2013.01); *A61K 47/34* (2013.01); *A61L 27/18* (2013.01); *C08J 3/24* (2013.01); *C08J 2379/04* (2013.01)

(58) Field of Classification Search
CPC ...... C08G 73/1092; C08J 3/24; C08J 2379/04
See application file for complete search history.

(56) References Cited

FOREIGN PATENT DOCUMENTS

| | | | |
|---|---|---|---|
| CN | 107281539 | * | 10/2017 |
| JP | 10-168184 A | | 6/1998 |

OTHER PUBLICATIONS

CN 107281539 machine translation (2017).*
JP 10 168184 machine translation (1998).*
Korean Office Action dated Mar. 30, 2020 in counterpart Korean Patent Application No. 10-2019-0010340 (5 pages in Korean).

* cited by examiner

*Primary Examiner* — Kuo Liang Peng
(74) *Attorney, Agent, or Firm* — NSIP Law

(57) ABSTRACT

Disclosed are a novel polymer compound containing multiple hydroxyl groups, a method for producing the same, and a complex having a crosslinked structure of the polymer compound. The polymer compound includes a repeating unit represented by a following Chemical Formula 1:

[Chemical Formula 1]

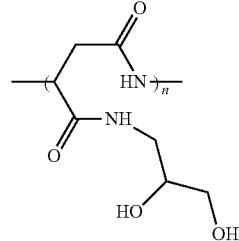

where in the Chemical Formula 1, n denotes an integer of 10 to 10,000.

12 Claims, 16 Drawing Sheets

POLYMER COMPOUNDS CONTAINING MULTIPLE HYDROXYL GROUPS, METHODS FOR PRODUCING THE SAME, AND COMPLEX CONTAINING THE SAME

CROSS-REFERENCE TO RELATED APPLICATIONS

This application claims the benefit under 35 U.S.C. § 119(a) of Korean Patent Application No. 10-2019-0010340 filed on Jan. 28, 2019, in the Korean Intellectual Property Office, the entire disclosure of which is incorporated herein by reference for all purposes.

BACKGROUND

1. Field

The present disclosure relates to a novel polymer compound containing multiple hydroxyl groups. More specifically, the present disclosure relates to a novel polymer compound containing multiple hydroxyl groups, a method for producing the same, and a complex having a crosslinked structure of the polymer compound.

2. Description of Related Art

Hydrophilic biocompatible polymers play an important role in biomedical and pharmaceutical fields. In particular, very flexible and hydrophilic polymers such as poly(ethylene glycol) (PEG), poly(vinyl alcohol) (PVA), poly(2-hydroxyethyl methacrylate) (PHEMA), poly(hydroxyethyl acrylate) (PHEA) are directly and closely related to the hydrophilic biocompatible polymers. These polymers show many interesting properties and have no biotoxicity and are widely applied in the pharmaceutical and biomedical fields.

Recently, linear and hyper-branched polyglycidol (PGL) polymers has high hydrophilicity due to strong intermolecular bonds between water and hydroxy or ether of the polymer, or intramolecular hydrogen bonds, and, thus, in recent years, is emerging as an attractive alternative to PEG in a wide range of applications. Further, polymers rich in hydroxy functional groups in a backbone have an advantage that they may be easily modified using useful molecules and biomolecules to provide versatile biomaterials.

Increasing demand for suitable polymers that may meet a variety of biomaterial properties is driving development of new types of polymer materials that may replace existing materials. Accordingly, there is a need for research and development of new polymer materials.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a polyaspartamide-based polymer compounds containing multiple hydroxyl groups.

Another purpose of the present disclosure is to provide a method for producing a polyaspartamide-based polymer compound containing multiple hydroxyl groups.

Another purpose of the present disclosure is to provide a complex containing a polyaspartamide-based polymer compound containing multiple hydroxyl groups.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

In a first aspect of the present disclosure, there is provided a polymer compound containing multiple hydroxyl groups, the compound including a repeating unit represented by a following Chemical Formula 1:

[Chemical Formula 1]

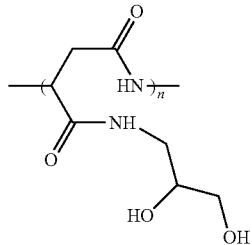

where in the Chemical Formula 1, n denotes an integer of 10 to 10,000.

In one implementation of the first aspect, the polymer compound is biocompatible and has a cell viability of 88% or greater at a dose of 15 mg or smaller thereof.

In one implementation of the first aspect, the polymer compound is capable of adhering to at least one of polymer, glass or metal.

In one implementation of the first aspect, the polymer compound has an adhesion strength of at least 350 KPa to at least one of glass or metal.

In a second aspect of the present disclosure, there is provided a complex including a crosslinked polymer compound, the polymer compound including a repeating unit represented by a following Chemical Formula 1:

[Chemical Formula 1]

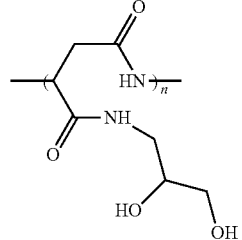

where in the Chemical Formula 1, n denotes an integer of 10 to 10,000.

In one implementation of the second aspect, the polymer compound is crosslinked via a boron ion or a trivalent iron ion.

In one implementation of the second aspect, the complex has a structure represented by a following Chemical Formula 2:

compound with each other, wherein the polymer compound includes a repeating unit represented by a following Chemical Formula 1:

[Chemical Formula 1]

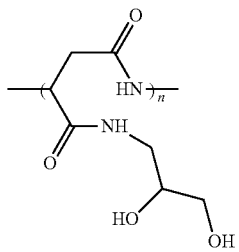

wherein in the Chemical Formula 1, n represents an integer of 10 to 10,000.

In one implementation of the third aspect, the method further comprises, after reacting the polysuccinimide and the amino propanediol-based compound with each other, freeze-drying a reaction product.

Effects of the present disclosure are as follows but are not limited thereto.

According to the present disclosure, the present disclosure may provide a novel poly(N-2,3-dihydroxypropyl aspartamide) (PDHPA) as a novel polyaspartamide derivative polymer containing plurality of hydroxyl groups.

According to the present disclosure, the polymer compound according to the present disclosure may be easily produced from an amino decomposition reaction of polysuccinimide and aminopropanediol, and thus may be economical in terms of producing.

In particular, the polymer compound according to the present disclosure has excellent characteristics of biodegradability, high water solubility, excellent biocompatibility, and strong adhesive ability.

Further, the polymer compound in accordance with the present disclosure has an amide backbone and two hydroxy functional groups in a side chain in each repeating unit, resulting in multiple hydroxyl groups in the polymer structure. Due to the unique chemical structure of the polymer in accordance with the present disclosure, the polymer compound according to the present disclosure may easily form a chemical bond or a physical bond with other component materials. Due to these characteristics, the polymer compound according to the present disclosure may function as a useful platform for constructing a complex such as hydrogels having dynamic reversibility and self-healing characteristics. In addition, the cross-linked hydrogel made of the polymer compound according to the present disclosure will be useful as biocompatible materials for a scaffold in tissue engineering, drug delivery, pharmaceuticals, bio separation membrane and metal nanoparticle production in a variety of biomedical applications.

In addition to the effects as described above, specific effects of the present disclosure are described together with specific details for carrying out the invention.

[Chemical Formula 2]

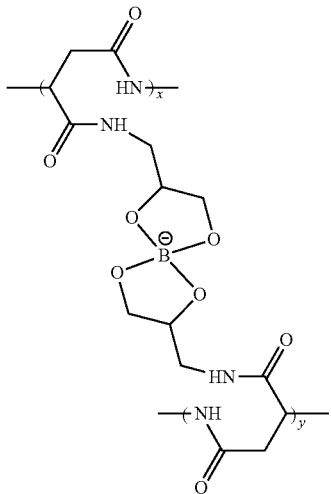

wherein in the Chemical Formula 2, each of x and y independently denotes an integer of 10 to 10,000.

In one implementation of the second aspect, the complex is an adhesive hydrogel having self-healing ability.

In one implementation of the second aspect, the polymer compound is crosslinked via a glutaraldehyde-based compound, a dialdehyde-based compound or polymeric aldehyde.

In one implementation of the second aspect, the complex has a structure represented by a following Chemical Formula 3:

[Chemical Formula 3]

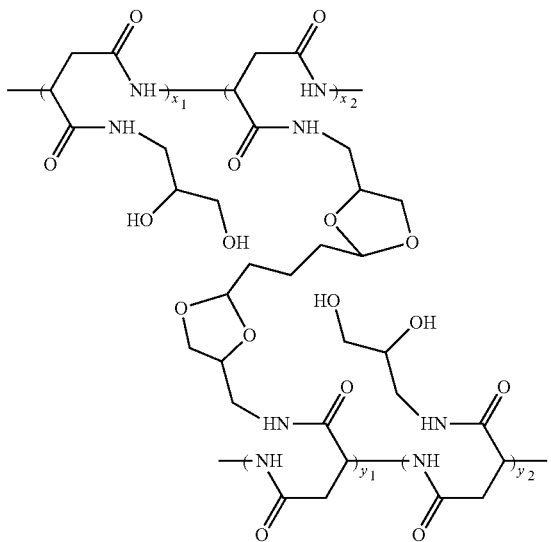

wherein in the Chemical Formula 3, each of x1, x2, y1 and y2 independently denotes an integer of 10 to 10,000.

In one implementation of the second aspect, the complex has a micro-porous structure including multiple micropores.

Figure 3:
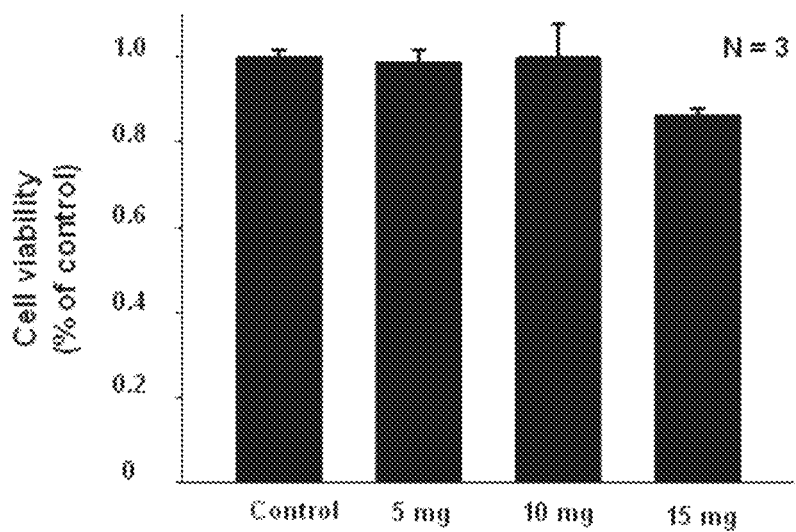

In a third aspect of the present disclosure, there is provided a method for producing a polymer compound containing multiple hydroxyl groups, the method comprising reacting polysuccinimide and an amino propanediol-based FIG. 3 illustrates biocompatibility of a polymer compound according to one embodiment of the present disclosure.

Figure 4:
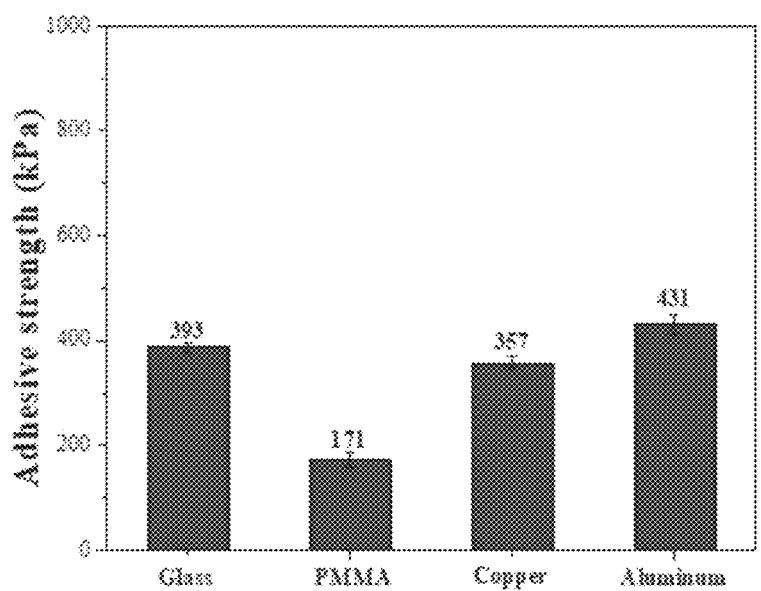

FIG. 4 illustrates adhesion of a polymer compound according to one embodiment of the present disclosure.

Figure 5:
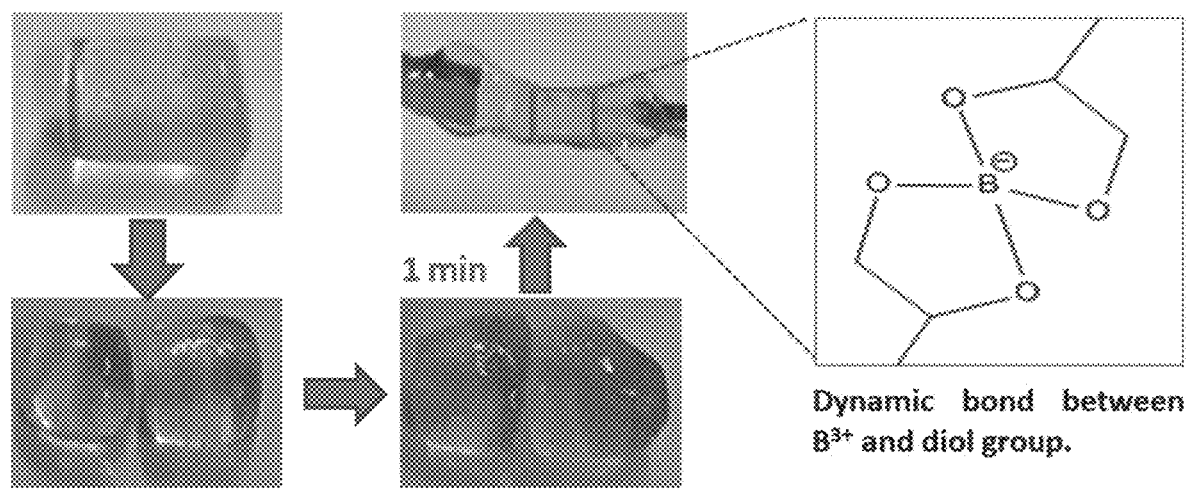

FIG. 5 is a diagram for describing a self-healing characteristic of a hydrogel according to an embodiment of the present disclosure.

Figure 6:
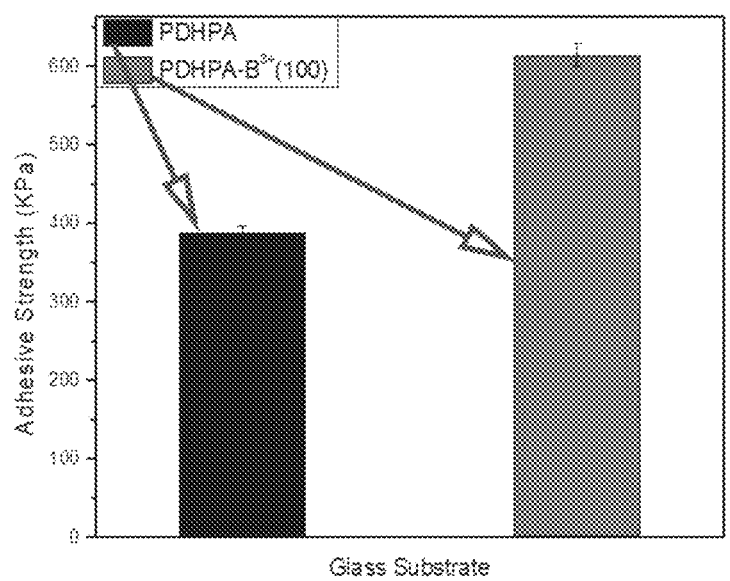

FIG. 6 is a diagram for describing an adhesion characteristic of a hydrogel according to an embodiment of the present disclosure.

Figure 7:
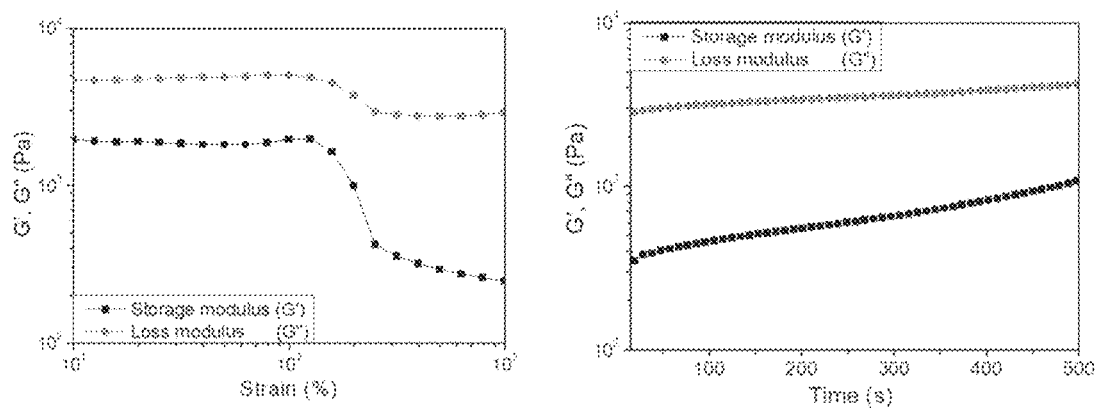

FIG. 7 illustrates a flow measurement result of a hydrogel according to an embodiment of the present disclosure.

Figure 8A:
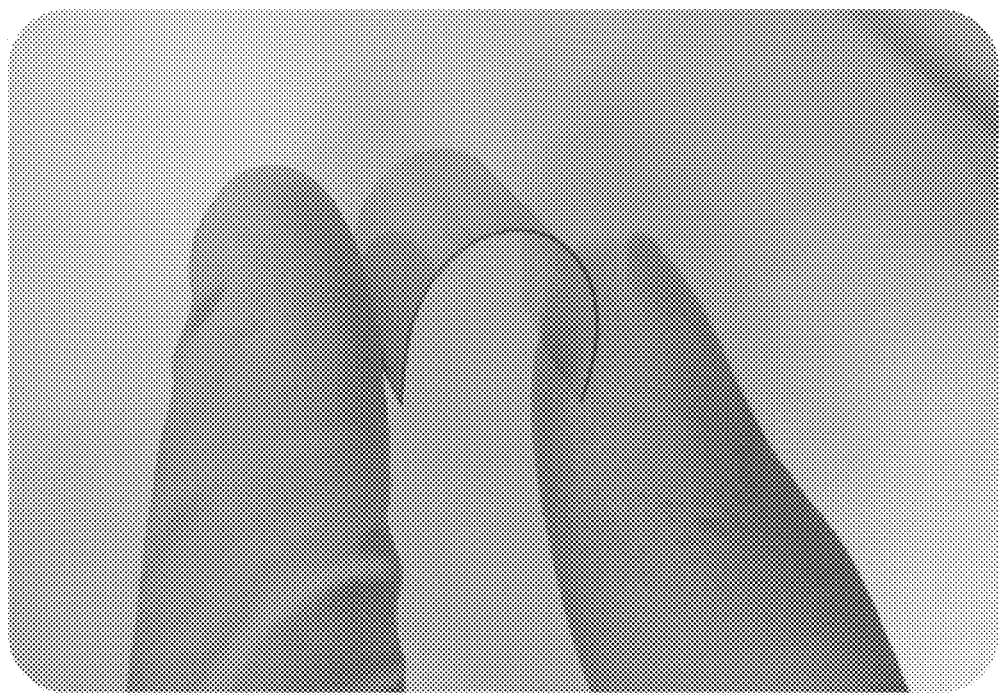
Figure 8B:
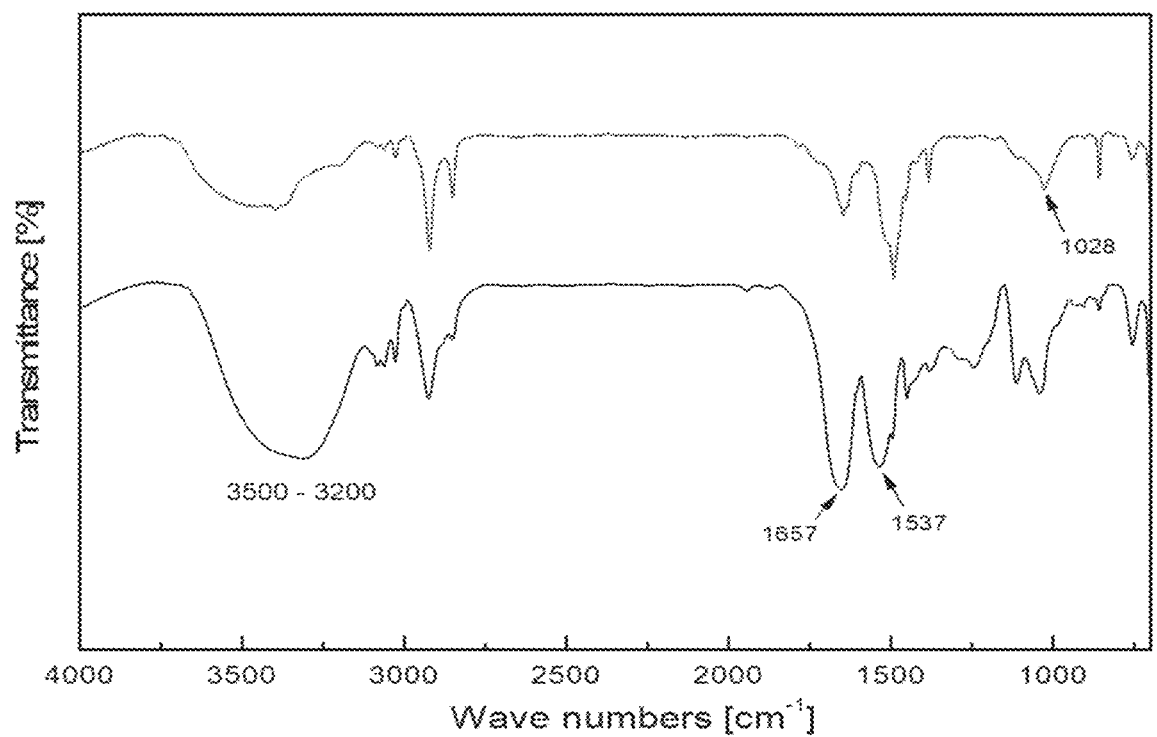
Figure 8C:
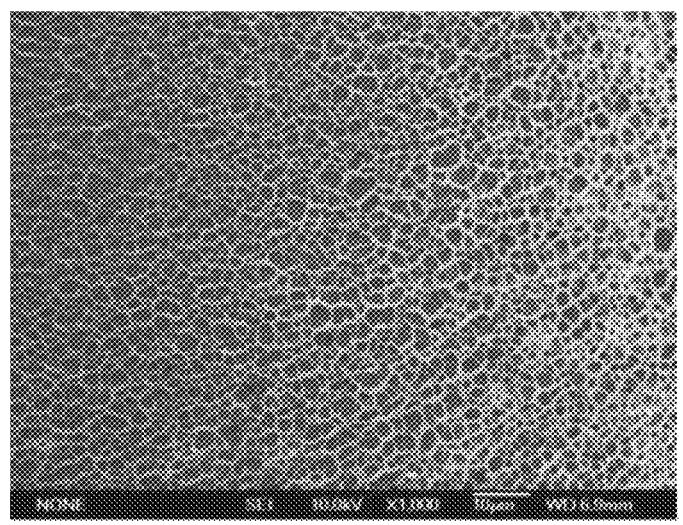
Figure 8C:
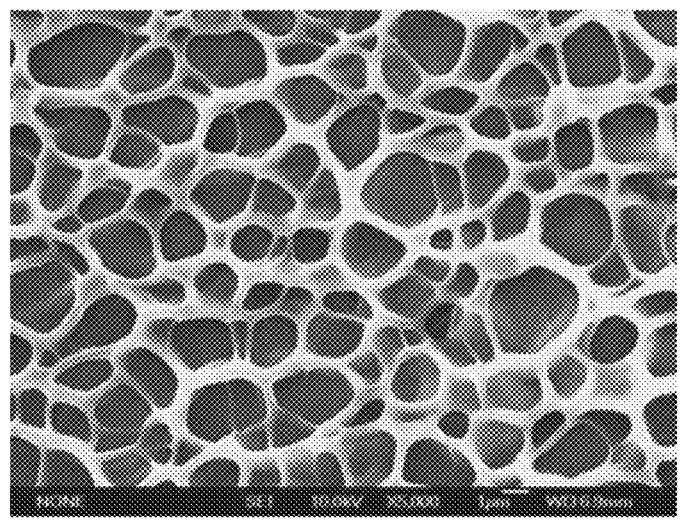

FIGS. 8A, 8B and 8C are a diagram for describing a structure of a PDHPA-GA gel membrane according to an embodiment of the present disclosure.

Figure 9:
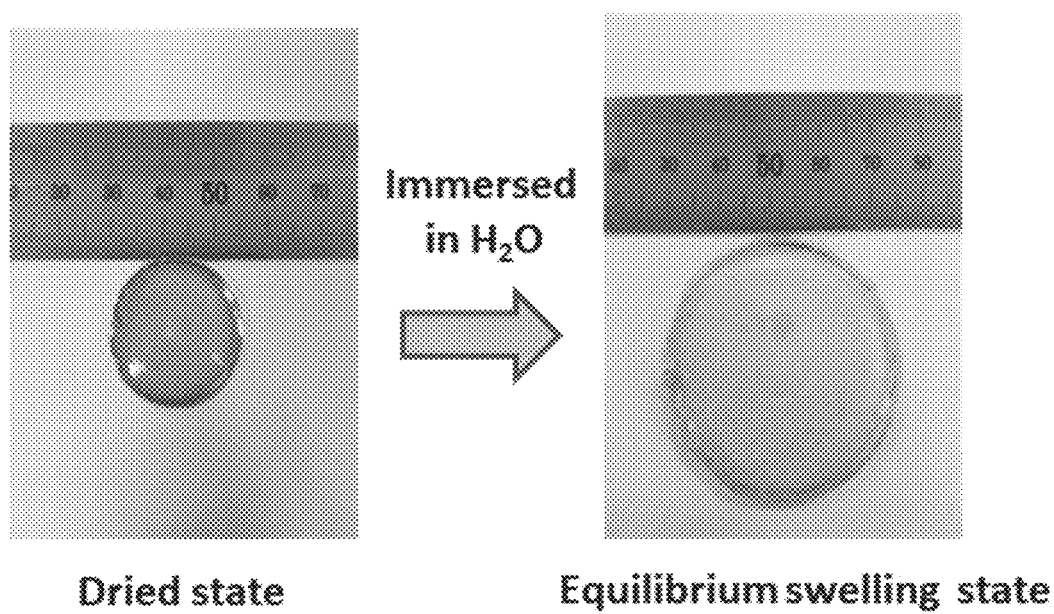

FIG. 9 illustrates a swelling characteristic of a gel membrane according to one embodiment of the present disclosure.

Figure 10:
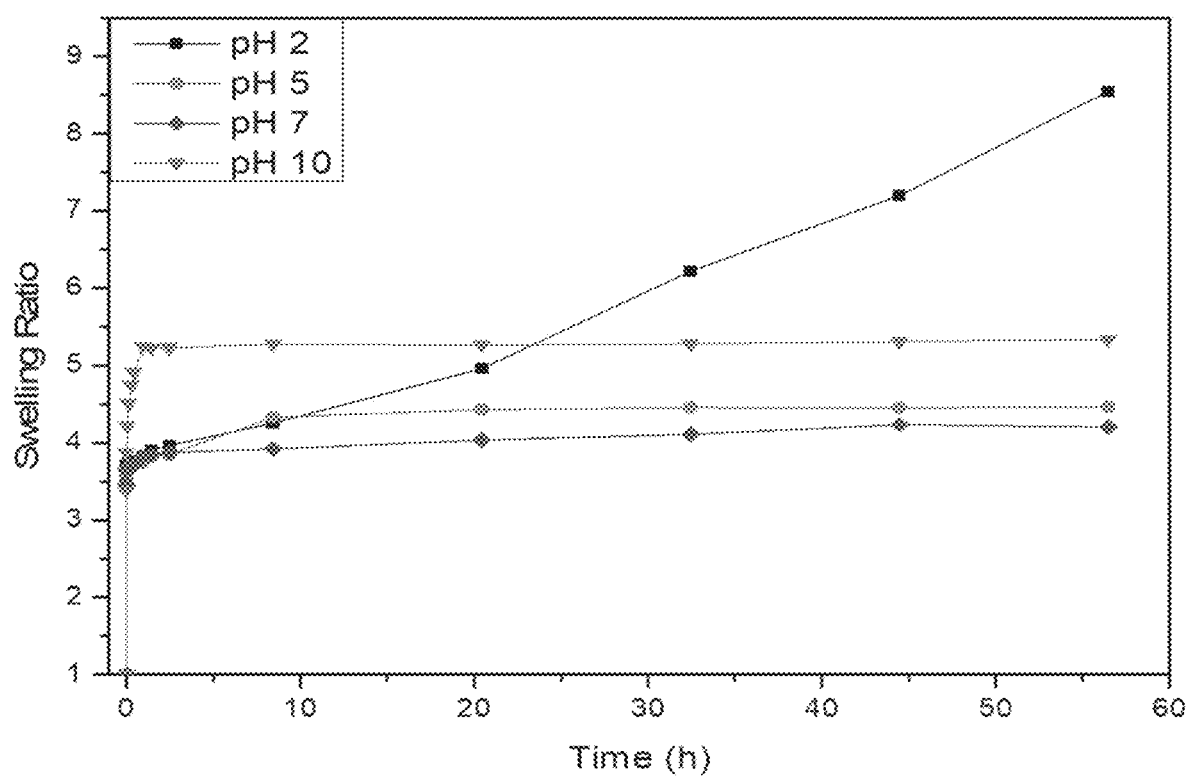

FIG. 10 is a diagram for describing a swelling characteristic of a gel membrane according to one embodiment of the present disclosure.

Figure 11:
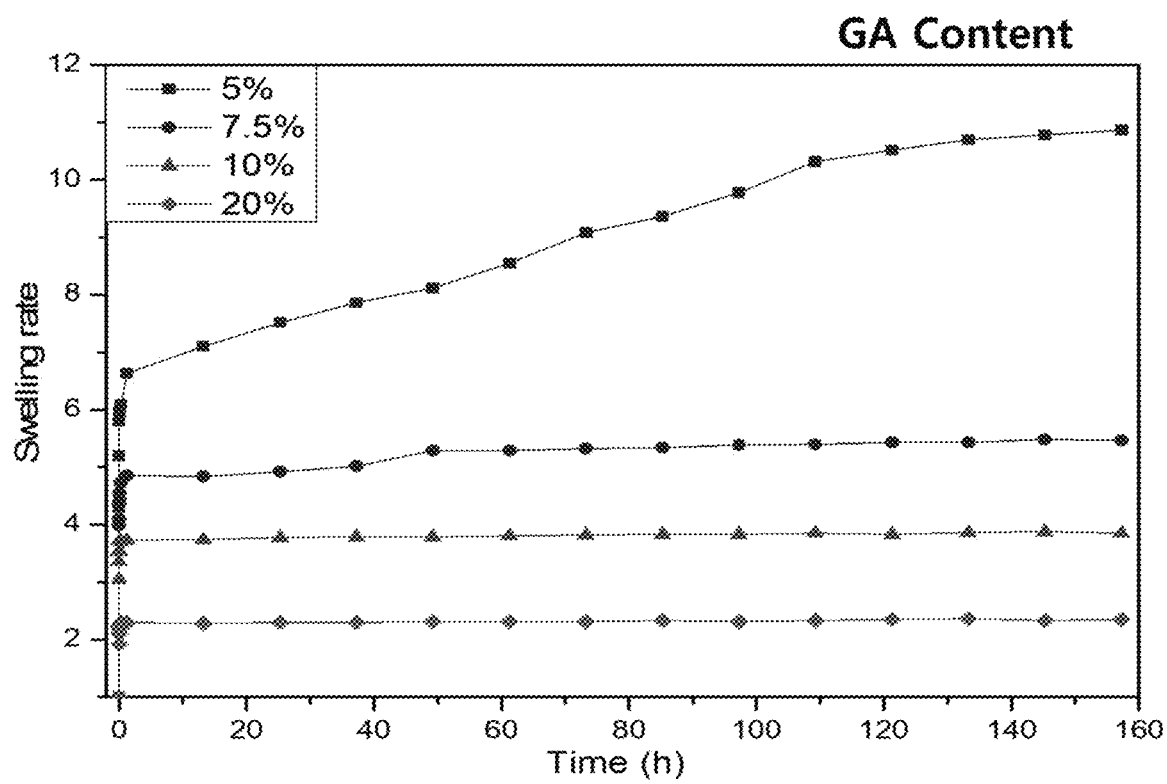

FIG. 11 is a diagram for describing a swelling characteristic of a gel membrane according to one embodiment of the present disclosure.

Figure 12:
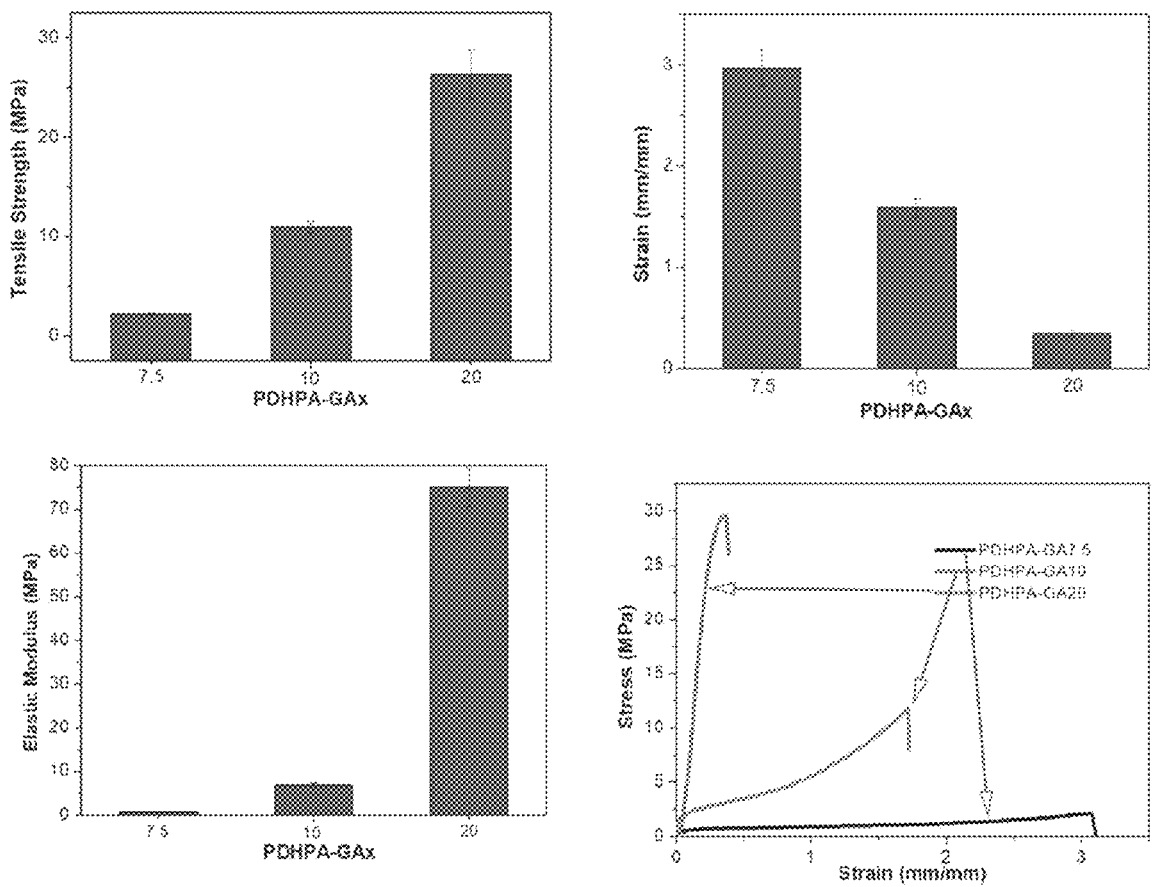

FIG. 12 is a diagram for describing mechanical characteristics of a PDHPA-GA gel membrane according to an embodiment of the present disclosure.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A polymer compounds according to the present disclosure includes a repeating unit represented by a following Chemical Formula 1.

[Chemical Formula 1]

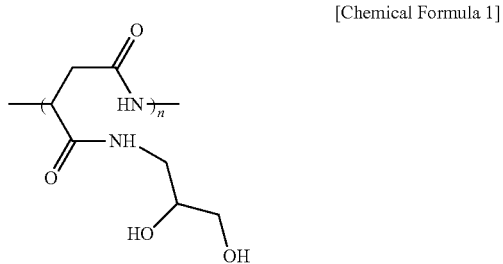

In the Chemical Formula 1, n represents an integer of 10 to 10,000.

The polymer compound according to the present disclosure is a polyaspartamide-based polymer with a structure having an amide backbone and similar to that of a protein and has a side chain including two hydroxyl groups in each repeating unit and thus contains multiple hydroxyls.

The polymer compound according to the present disclosure may be synthesized via an amino decomposition reaction of polysuccinimide and aminopropanediol. More specific description thereof will be described later with reference to Examples.

The polymer compound according to the present disclosure are highly water soluble, biodegradable, non-toxic, non-antigenic, biocompatible and has excellent adhesion characteristics with metal and inorganic adhered materials.

Further, the polymer compound according to the present disclosure has the structural characteristics of the amide backbone and the hydroxy-containing side chain and thus may easily achieve chemical or physical bonds with other component materials to form a complex.

In one example, the polymer compound according to the present disclosure may be cross-linked via metal ions such as boron ions to form a complex. In this connection, the complex has a structure represented by a following Chemical Formula 2.

[Chemical Formula 2]

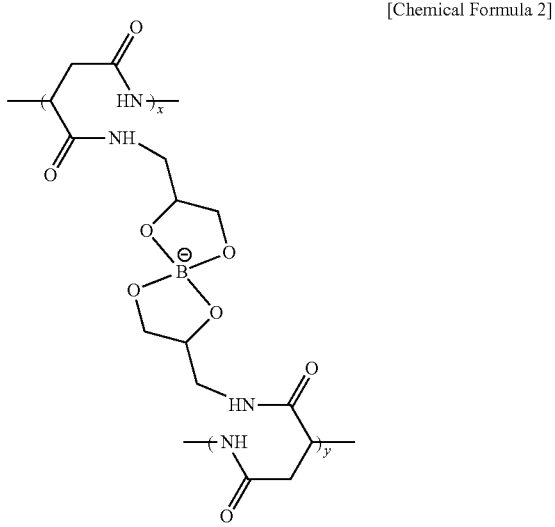

In the Chemical Formula 2, each of x and y is independently an integer of 10 to 10,000.

The complex is not only biocompatible and water soluble as in the polymer compound according to the present disclosure. The complex may have an improved adhesion characteristic compared to the polymer compound. The complex may have self-healing ability via a reversible kinetic bond between the metal and the hydroxy group. Further, the complex may be a swelling gel that absorbs water and expands.

Alternatively, the polymer compound according to the present disclosure may be cross-linked via a glutaraldehyde-based compound to form a complex. In this connection, the complex has a structure expressed as a following Chemical Formula 3.

[Chemical Formula 3]

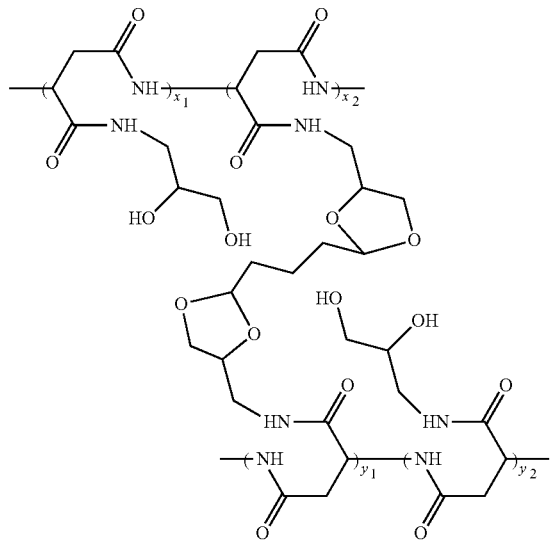

In the Chemical Formula 3, each of x1, x2, y1 and y2 is independently an integer of 10 to 10,000.

The complex crosslinked via the glutaraldehyde-based compound has a dual network structure achieved via covalent bonds and reversible dynamic crosslinking between the crosslinking agent and the polymer. The complex may be a porous material having a micro-porous structure.

That is, the polymer compound according to the present disclosure may be cross-linked via a metal ion or a cross-linking agent such as a glutaraldehyde-based compound to form a complex. The complex in accordance with the present disclosure is water based swelling and biocompatible, and has an excellent adhesion characteristic. Further, the complex in accordance with the present disclosure may be transparent and flexible.

Further, the complex according to the present disclosure may take many forms such as films or particles. Depending on an amount of the crosslinking agent added thereto, the complex may have a variety of mechanical characteristics and thus may be produced to have a shape and characteristics suitable for an intended use.

For example, the present disclosure complex may be used in the biomedical field, and may constitute a scaffold, a drug delivery carrier, a bio separation membrane and the like.

A more detailed description of the polyaspartamide-based polymer containing the plurality of hydroxyl groups in accordance with the present disclosure, a method for producing the same, a complex including the same, and a characteristic thereof will be described below with reference to specific Examples. However, the present disclosure is limited thereto.

Present Example 1. Producing of Polymer Compound According to the Present Disclosure (1) Synthesis of Polysuccinimide (PSI)

Polysuccinimide (PSI) was produced and purified via thermal condensation polymerization of aspartic acid monomers using an acid as a catalyst. First, L-aspartic acid (30 g) and o-phosphoric acid (30 g) were put in a round bottom flask in a 1:1 weight ratio and mixed with each other at room temperature. Thereafter, while a pressure was gradually changed from an atmospheric pressure to −74 cmHg and a temperature was gradually changed from room temperature to 180° C., reaction of the mixture was initiated and lasted over 1 hour.

Then, the above process ended, and, subsequently, the reaction was maintained at 180° C. for 5 hours under a reduced pressure. Thereafter, the reaction mixture was cooled to room temperature and DMF was added thereto to dissolve the product. The obtained aqueous solution was precipitated using excessive ethanol and was washed several times with distilled water until the pH thereof reached 7 to completely remove monomers that did not react with remaining o-phosphoric acid. The product as obtained was then dried in a vacuum oven at 60° C. for 3 days to synthesize white powdery PSI.

(2) Synthesis of Polymer Compound

We dissolved 0.97 g of PSI in 30 ml N, N-dimethylformaldehyde (DMF), and then slowly dropped 1.17 ml of 3-amino-1,2-propanediol (150 mol % relative to PSI) into the stirred PSI solution. After reacting at room temperature for 3 days, the final reactant was dialyzed and lyophilized. Thus, the polyaspartamide-based polymer compound containing multiple hydroxyl groups according to Present Example 1 of the present disclosure, that is, poly(N-2,3-dyhidroxypropyl aspartamide) (hereinafter, referred to as PDHPA) was produced.

In this connection, a reaction yield was 79 to 86%. An intrinsic viscosity (η) of PDHPA was measured with an Ostwald viscometer to obtain a value of 33.26 dL/g.

The L-aspartic acid (98%), o-phosphoric acid (99%), 3-amino-1,2-propanediol, N,N-dimethylformaldehyde (DMF) and ethanol (95%) as used in the synthesis were purchased from Sigma Aldrich. All of the components as purchased were used without further purification.

The synthesis process of PDHPA according to Present Example 1 of the present disclosure may be expressed as a following Reaction Formula 1.

[Reaction Formula 1]

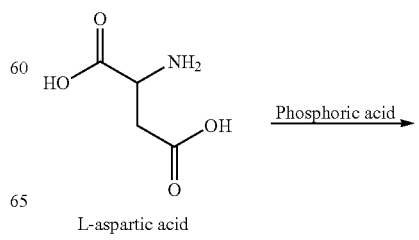

L-aspartic acid

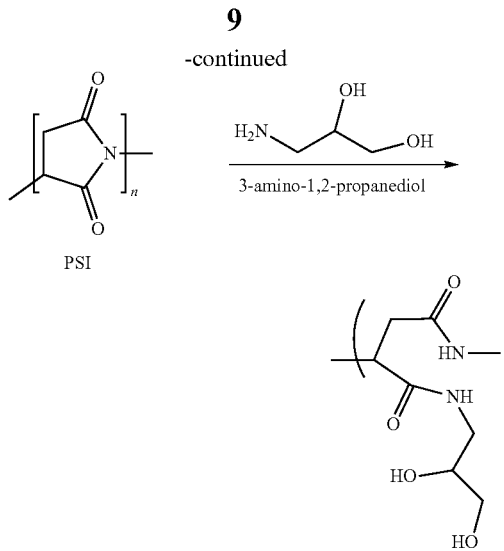

Characteristic-1: Structure Analysis

A FT-IR spectrum and 1H-NMR spectrum of the polymer compound according to Present Example 1 of the present disclosure were identified. The results are shown in FIG. 1.

FIG. 1 is a diagram for illustrating the FT-IR spectrum and $^1$H-NMR spectrum of a polymer compound according to an embodiment of the present disclosure.

Figure 1A:
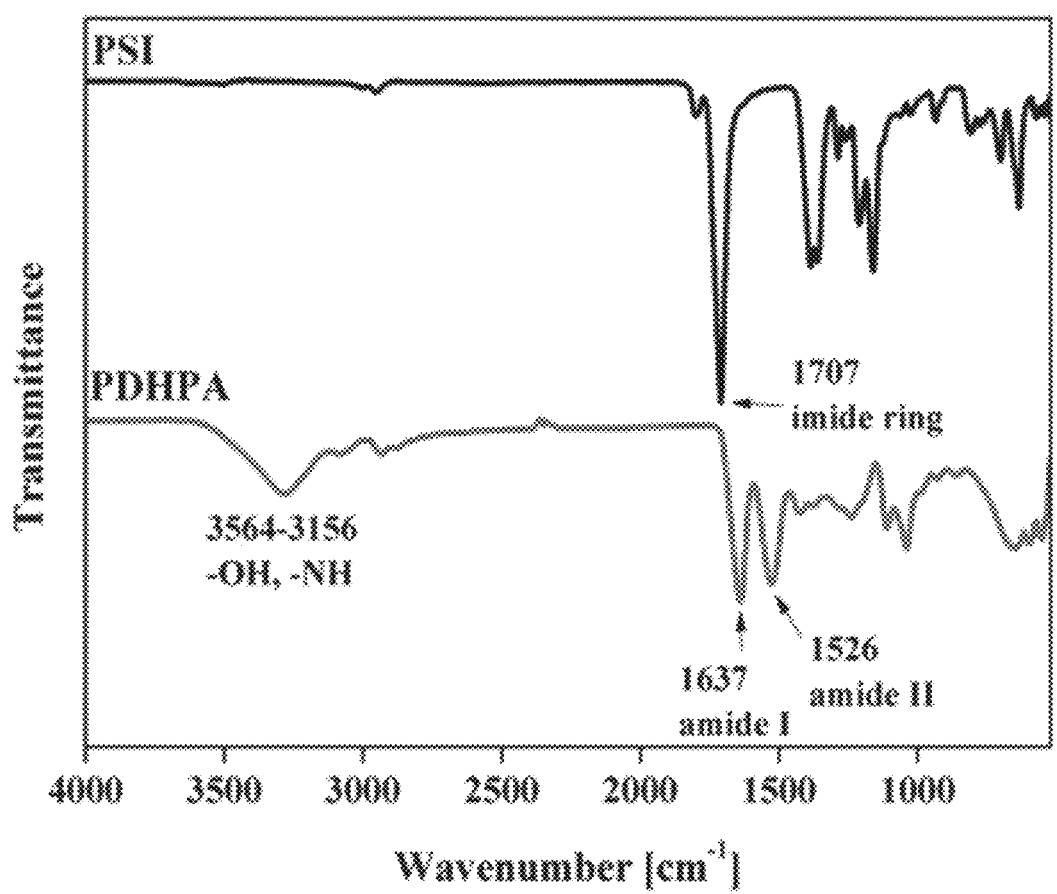
FIGS. 1A and 1B are a diagram for describing a FT-IR spectrum and a $^1$H-NMR spectrum of a polymer compound according to an embodiment of the present disclosure.
Figure 1B:
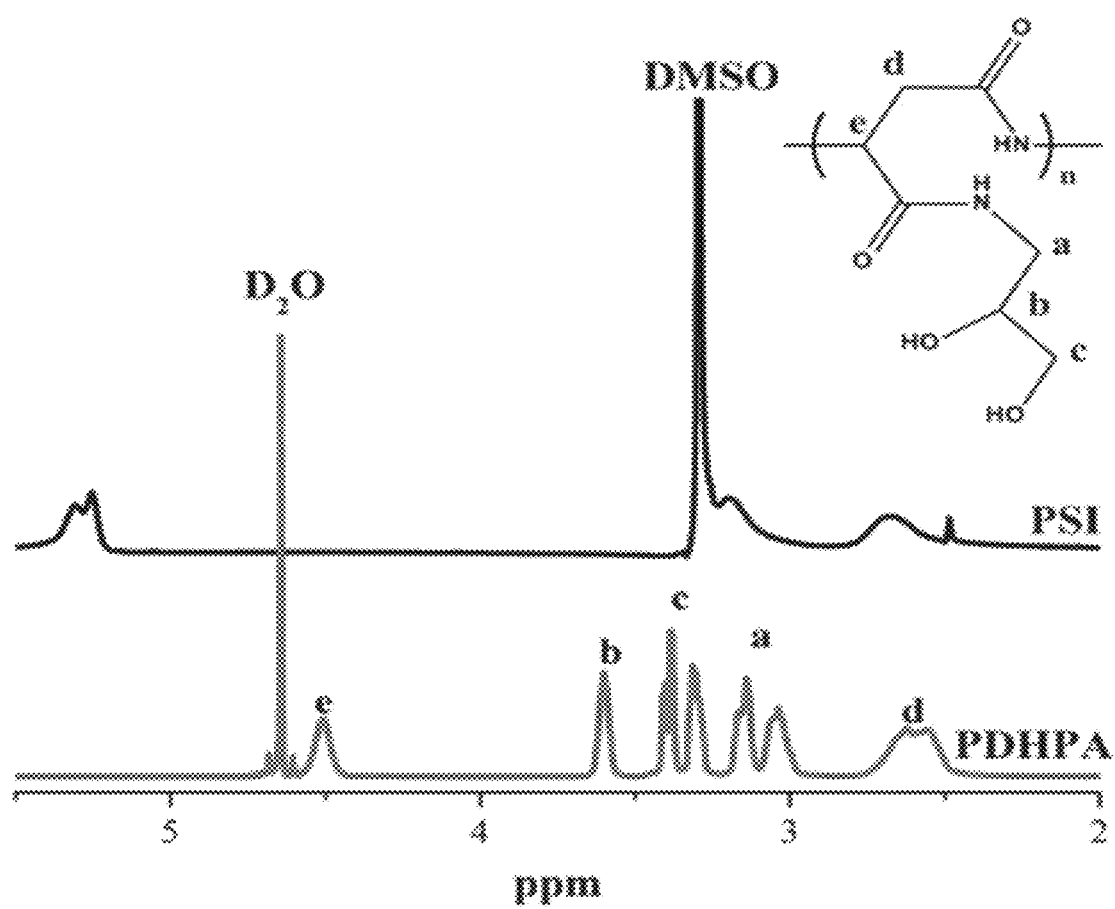

FIG. 1A shows the FT-IR spectrum of PSI ('A' in FIG. 1) and PDHPA ('B' in FIG. 1). FIG. 1B shows the 1H-NMR spectrum thereof.

First, referring to FIG. 1A, it may be seen that a characteristic band at 1706.7 cm-1 due to an imide ring of the PSI is identified. In one example, it may be seen that in the PDHPA, an absorption peak associated with an imide bond disappears, and amide I (1656.6 cm-1) and amide II (1537.2 cm-1) absorption bands appear, a broad absorption band of —OH and —NH groups appears in a range of 3564 to 3156 cm-1.

Referring to FIG. 1B, compared with the PSI spectrum, the 1H-NMR spectrum of the PDHPA shows a hydrogen peak of a dihydroxypropyl group introduced at 3.1 ppm and 3.6 ppm, and a succinimide ring methine hydrogen peak of PSI of 5.3 ppm has disappeared.

That is, it may be identified that the polyaspartamide-based polymer compound having a new structure having a dihydroxypropyl group according to the present disclosure was synthesized.

Characteristic-2: DSC and TGA

DSC and TGA were performed to confirm the thermal behavior and degradation characteristics of PDHPA. In DSC analysis, a temperature of a sample was raised from 20° C. to 200° C. under a nitrogen condition at a rate of 10° C. min-1. In TGA analysis, the sample was heated at a rate of 10° C. min-1 from 25° C. to 600° C. under a nitrogen condition. Each result is shown in FIG. 2.

FIG. 2 is a diagram for describing the thermal behavior and decomposition characteristics of a polymer compound according to an embodiment of the present disclosure.

Figure 2A:
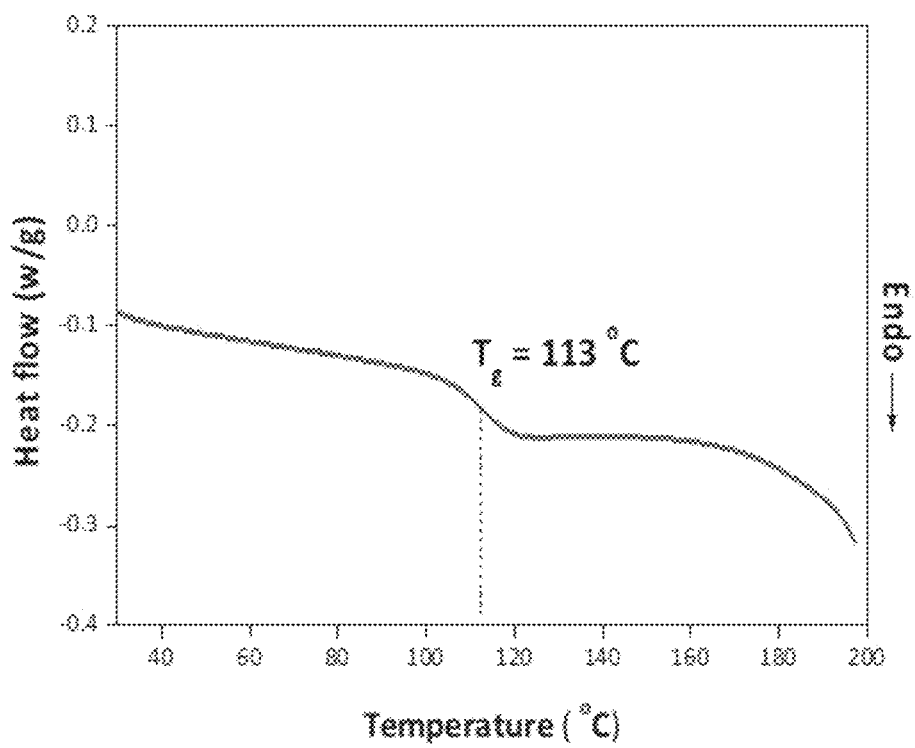
FIGS. 2A and 2B are a diagram for describing thermal behavior and decomposition characteristics of a polymer compound according to an embodiment of the present disclosure.
Figure 2B:
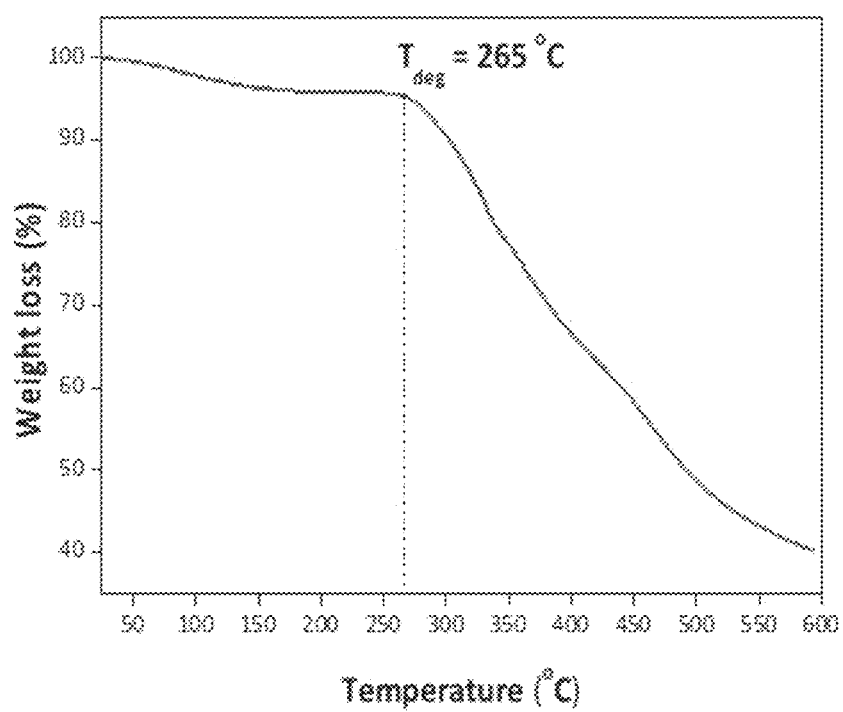

FIG. 2A shows the DCS analysis result of PDHPA in accordance with the present disclosure. FIG. 2B shows the TGA result thereof.

Referring to FIG. 2A, it may be seen from the result of DSC analysis that a glass transition temperature (Tg) may be identified at a temperature of 113° C. in PDHPA.

Referring to FIG. 2B, it may be identified from the TGA result that the decomposition starts around 265° C. (Tdeg: about 265° C.).

Characteristic-3: Biocompatibility

Cytotoxicity experiments were conducted to identify the biocompatibility of PDHPA. The results are shown in FIG. 3.

FIG. 3 illustrates biocompatibility of a polymer compound according to one embodiment of the present disclosure.

Referring to FIG. 3, it may be seen from the results of the cytotoxicity experiment that a cell viability of more than 88% was identified for 5 mg, 10 mg, 15 mg PDHPA. These results suggest that PDHPA may be used as a non-toxic biocompatible polymer in various bio-application applications.

Characteristic-4: Adhesion

In order to describe the adhesion characteristics of PDHPA, adhesion thereof to various adhered materials was identified. The results are shown in FIG. 4.

FIG. 4 illustrates adhesion of a polymer compound according to one embodiment of the present disclosure.

Referring to FIG. 4, PDHPA shows higher adhesion to metal adhered materials such as aluminum, copper, and inorganic adhered materials such as glass than to polymer adhered materials. The excellent adhesion characteristic of PDHPA may be due to strong intermolecular attraction including hydrogen bonds based on the long chain structure of the polyaspartamide having the plurality of hydroxyl groups as substituents.

In other words, according to the present disclosure, it may be seen that the PDHPA as the polyaspartamide-based polymer having a new structure and containing many hydroxy groups in the side chain via the amino decomposition reaction between the polysuccinimide as a precursor and the aminopropanediol based compound may be produced.

Further, the novel polyaspartamide-based polymer according to the present disclosure has biodegradability, high water solubility and excellent biocompatibility and strong adhesion characteristic. Due to those characteristics, the novel polyaspartamide-based polymer according to the present disclosure may be applicable to various biomedical fields.

In addition, the polymer compound according to the present disclosure has a unique chemical structure having a stable chemical amide backbone and containing the plurality of hydroxy groups in the side chain, so that the novel polymer compound may be easily combined with other molecules, thereby to form a hydrogel or a composite gel having a dynamic reversibility and a self-healing characteristic.

Present Example 2. Producing of Hydrogel According to the Present Disclosure An aqueous solution containing the polymer compound produced according to the Present Example 1 was reacted with boronic acid (H3BO3) at a reaction condition of pH 8 and 25° C. Thus, a hydrogel (hereinafter, referred to as PDHPA-B hydrogel) according to Present Example 2 of the present disclosure was produced.

The synthesis process of PDHPA-B hydrogel according to Present Example 2 of the present disclosure may be expressed as a following Reaction Formula 2.

[Reaction Formula 2]

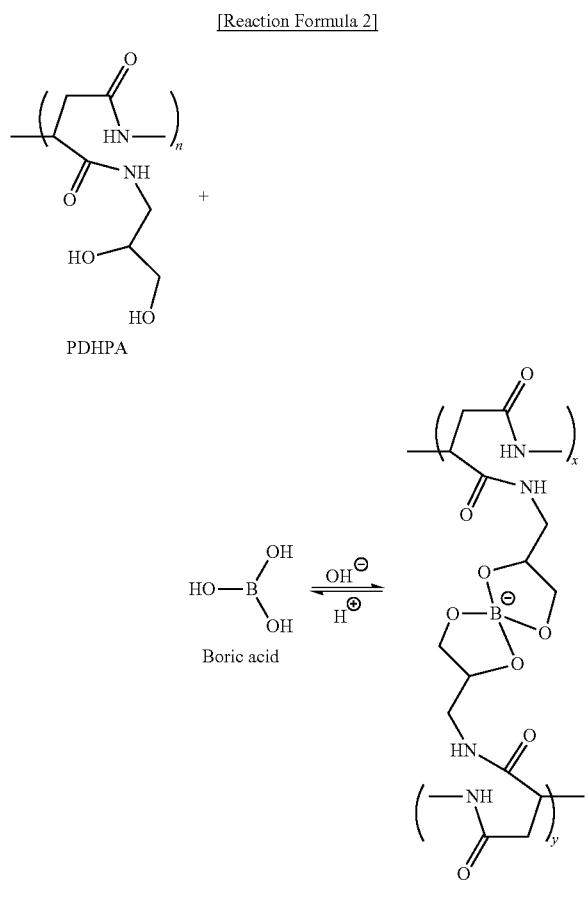

Characteristic-1: Self-Healing

We identified the self-healing characteristic of PDHPA-B hydrogel in accordance with the present disclosure. The results are shown in FIG. 5.

FIG. 5 is a diagram for describing a self-healing characteristic of a hydrogel according to an embodiment of the present disclosure.

Referring to FIG. 5, we bisected the PDHPA-B hydrogel in accordance with the present disclosure and contacted cut surfaces of two bisected portions with each other. In 1 minute, the two portions of the hydrogel were bonded to each other. That is, this shows that the PDHPA-B hydrogel according to the present disclosure is self-healing even after complete cleavage. This may be due to the kinetic bond between boron ions and diol groups in the hydrogel.

Characteristic-2: Adhesion

Further, we identified the adhesion of PDHPA-B hydrogel according to the present disclosure onto an organic substrate. The results are shown in FIG. 6.

FIG. 6 is a diagram for describing the adhesion characteristic of the hydrogel according to an embodiment of the present disclosure.

Referring to FIG. 6, it may be seen that the adhesion characteristic of the PDHPA-B hydrogel in accordance with the present disclosure is further improved compared to the PDHPA according to the present disclosure.

In other words, the adhesion characteristic of PDHPA according to the present disclosure is excellent, but the adhesion characteristic of the PDHPA-B hydrogel cross-linked via the boron is superior to the adhesion characteristic of PDHPA according to the present disclosure.

Characteristic-3: Rheological Properties Measurement (Rheometry)

The rheological properties of the PDHPA-B hydrogel according to the present disclosure were measured. The results are shown in FIG. 7.

FIG. 7 is a diagram for describing the rheological properties measurement results of a hydrogel according to an embodiment of the present disclosure.

Referring to FIG. 7, the measurement results of the rheological properties of the PDHPA-B hydrogel according to the present disclosure shows that the PDHPA-B hydrogel according to an embodiment of the present disclosure has a fast self-healing ability and strong adhesion characteristic based on the reversible kinetic coupling between di-hydroxy pendants and boron in the PDHPA structure.

Present Example 3. Producing of Gel Membrane According to the Present Disclosure After reacting a solution containing the polymer compound produced according to the Present Example 1 with glutaraldehyde (GA) at 60° C. for 6 hours, the reaction product was cast to a glass mold, and then the molded product was washed to produce a gel membrane (hereinafter referred to as PDHPA-GA gel membrane) according to Present Example 3 of the present disclosure.

The synthesis process of PDHPA according to Present Example 3 of the present disclosure may be expressed as a following Reaction Formula 3.

[Reaction Formula 3]

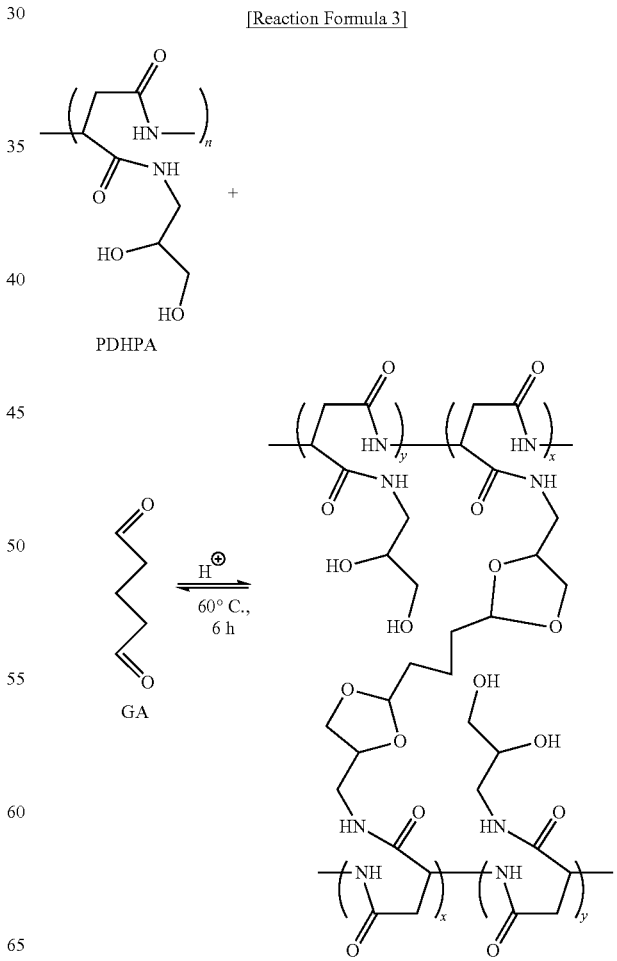

Characteristic-1: Structure Analysis

A FT-IR spectrum and surface SEM image of the PDHPA-GA gel membrane according to Present Example 3 of the present disclosure were taken. The results are shown in FIG. 8.

FIG. 8 is a diagram for illustrating the structure of the PDHPA-GA gel membrane according to an embodiment of the present disclosure.

FIG. 8A is a photograph of the PDHPA-GA gel membrane in accordance with the present disclosure. FIG. 8B is a diagram for describing the FT-IR spectrum thereof. FIG. 8C shows a SEM image of a surface thereof.

Referring to FIG. 8, it may be seen that each of the gel membrane produced using GA as a crosslinking agent according to the present disclosure and the PDHPA polymer compound according to the present disclosure has a uniform micro-porous structure.

Characteristic-2: Swelling Characteristic

The swelling characteristic of the PDHPA-GA gel according to the present disclosure was identified. The results are shown in FIG. 9.

FIG. 9 illustrates a swelling characteristic of a gel membrane according to one embodiment of the present disclosure.

Referring to FIG. 9, the result shows that the PDHPA-GA gel membrane according to the present disclosure swells when being immersed in water.

(1) Swelling Characteristic Depending on pH

We identified the swelling characteristic according to pH condition. The results are shown in FIG. 10.

FIG. 10 is a diagram for describing the swelling characteristic of the gel membrane according to one embodiment of the present disclosure.

Referring to FIG. 10, at pH 2, the swelling ratio increased over time. However, at a condition above pH 5, the swelling ratio was constant over time. As the pH increases, the swelling ratio tends to decrease. This means that the gel according to the present disclosure is pH sensitive.

(2) Swelling Characteristic Depending on GA Content

We identified the swelling characteristic based on the content of the crosslinking agent (GA). The results are shown in FIG. 11.

FIG. 11 is a diagram for describing the swelling characteristic of the gel membrane according to one embodiment of the present disclosure.

Referring to FIG. 11, it may be seen that as the content of the crosslinking agent exceeds 5%, the swelling ratio decreases over time.

Characteristic-3: Mechanical Characteristic

We identified the mechanical characteristics of PDHPA-GAx (x refers to a percentage (%) of added GA) gel membrane depending on the content of the crosslinking agent (GA). The results are shown in FIG. 12.

FIG. 12 is a diagram for describing the mechanical characteristics of PDHPA-GA gel membrane according to an embodiment of the present disclosure.

Referring to FIG. 12, it may be seen that the PDHPA-GA gel according to the present disclosure has various mechanical strengths depending on the amount of crosslinking agent as added thereto.

That is, it may be seen that the PDHPA-GA gel membrane according to the present disclosure has a dual network structure due to covalent bonds and reversible dynamic crosslinking between the crosslinking agent and the PDHPA polymer and has a micro-porous structure having multiple micro pores. Further, it may be identified that the gel membrane according to the present disclosure exhibits various mechanical characteristics depending on the amount of crosslinking agent as added thereto and has the pH sensitivity. Due to those characteristics, the gel membrane according to the present disclosure may be applicable to a variety of biological and biomedical applications, including bio-separation technology.

Although the present disclosure has been described above with reference to the preferred embodiments of the present disclosure, those skilled in the art will appreciate that various modifications and changes may be made in the present disclosure without departing from the spirit and scope of the present disclosure set forth in the following claims.

What is claimed is:

1. A complex including a crosslinked polymer compound, the polymer compound including a repeating unit represented by a following Chemical Formula 1:

[Chemical Formula 1]

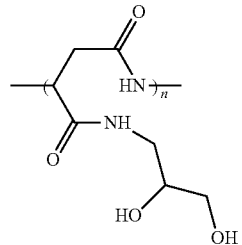

where in the Chemical Formula 1, n denotes an integer of 10 to 10,000, and further including a crosslinking agent that comprises a boron ion, a trivalent iron ion, a glutaraldehyde-based compound, a dialdehyde-based compound, or polymeric aldehyde.

2. The complex of claim 1, wherein the polymer compound is crosslinked via a boron ion or a trivalent iron ion.

3. The complex of claim 2, wherein the complex has a structure represented by a following Chemical Formula 2:

[Chemical Formula 2]

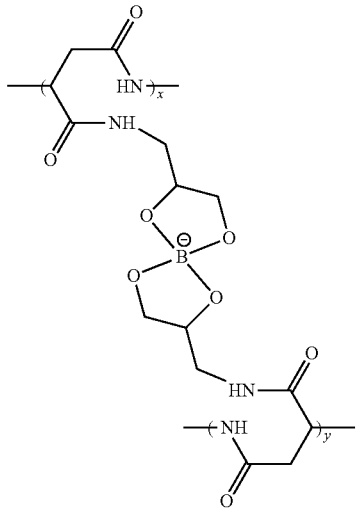

wherein in the Chemical Formula 2, each of x and y independently denotes an integer of 10 to 10,000.

4. The complex of claim 2, wherein the complex is an adhesive hydrogel having self-healing ability.

5. The complex of claim 1, wherein the polymer compound is crosslinked via a glutaraldehyde-based compound, a dialdehyde-based compound or polymeric aldehyde.

6. The complex of claim 5, wherein the complex has a structure represented by a following Chemical Formula 3:

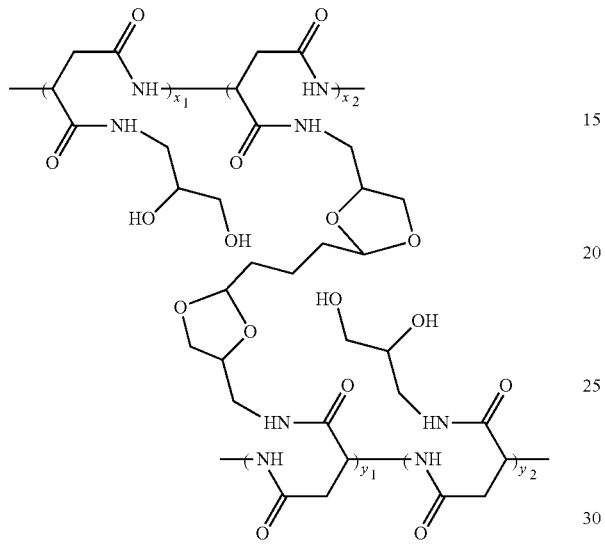

[Chemical Formula 3]

wherein in the Chemical Formula 3, each of $x_1$, $x_2$, $y_1$ and $y_2$ independently denotes an integer of 10 to 10,000.

7. The complex of claim 5, wherein the complex has a micro-porous structure including multiple micropores.

8. The complex of claim 1, wherein the polymer compound is biocompatible and has a cell viability of 88% or greater at a dose of 15 mg or smaller thereof.

9. The complex of claim 1, wherein the polymer compound is capable of adhering to at least one of polymer, glass or metal.

10. The complex of claim 1, wherein the polymer compound has an adhesion strength of at least 350 KPa to at least one of glass or metal.

11. A method for producing a polymer compound containing multiple hydroxyl groups, the method comprising reacting polysuccinimide and an amino propanediol-based compound with each other, wherein the polymer compound includes a repeating unit represented by a following Chemical Formula 1:

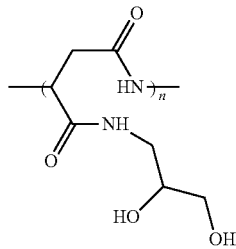

[Chemical Formula 1]

wherein in the Chemical Formula 1, n represents an integer of 10 to 10,000, and wherein the method further comprises, after reacting the polysuccinimide and the amino popanediol-based compound with each other, freeze-drying a reaction product.

12. A method for producing a complex including a polymer compound containing multiple hydroxyl groups, the method comprising:

reacting polysuccinimide and an amino propanediol-based compound with each other to produce the polymer compound, wherein the polymer compound includes a repeating unit represented by a following Chemical Formula 1:

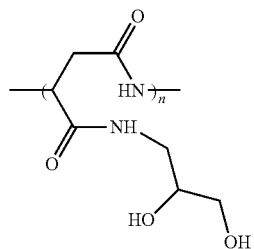

[Chemical Formula 1]

wherein in the Chemical Formula 1, n represents an integer of 10 to 10,000; and crosslinking the polymer compound with a crosslinking agent that comprises a boron ion, a trivalent iron ion, a glutaraldehyde-based compound, a dialdehyde-based compound, or polymeric aldehyde.

* * * * *